United States Patent [19]

Brooks

[11] 4,357,113
[45] Nov. 2, 1982

[54] LIQUID CONTAINER LEAKAGE DETECTION METHOD AND SYSTEM

[76] Inventor: Wahner E. Brooks, 2855 S. Madison Ave., Yuma, Ariz. 85364

[21] Appl. No.: 149,802

[22] Filed: May 14, 1980

[51] Int. Cl.³ ...................... G01N 25/72; G01M 3/18
[52] U.S. Cl. ...................................... 374/4; 340/605; 346/33 TP; 374/114
[58] Field of Search ............................ 73/40.5 R, 49.2; 116/DIG. 14

[56] References Cited

U.S. PATENT DOCUMENTS

| | | | |
|---|---|---|---|
| 2,708,896 | 5/1955 | Smith et al. | 116/DIG. 14 |
| 3,029,628 | 4/1962 | Minter | 73/27 |
| 3,217,550 | 11/1965 | Birman | 73/432 R |
| 3,375,702 | 4/1968 | Birman | 73/40 |
| 3,874,222 | 4/1975 | Ladd et al. | 73/40.5 R |
| 3,922,640 | 11/1975 | Ruof | 340/57 |
| 3,936,839 | 2/1976 | Brooks | 346/1.1 |
| 3,967,256 | 6/1976 | Galatis | 73/49.2 X |
| 4,095,462 | 6/1978 | Goto | 73/27 R X |
| 4,122,720 | 10/1978 | Podl | 340/57 X |

FOREIGN PATENT DOCUMENTS

| | | | |
|---|---|---|---|
| 2101717 | 12/1979 | Fed. Rep. of Germany | 73/49.2 |
| 2311292 | 12/1974 | France | 73/49.2 |
| 52-34777 | 3/1977 | Japan | 73/49.2 |
| 54-133201 | 10/1979 | Japan | 73/40 |

Primary Examiner—Daniel M. Yasich
Attorney, Agent, or Firm—Nathan Edelberg; Robert P. Gibson; Saul Elbaum

[57] ABSTRACT

The apparatus and method of the present invention are particularly adapted to monitor for leaks from a fluid container which is situated in a porous or semiporous medium, such as earth. A series of sensors is placed in the medium at a position which would intercept the path of fluid leaking from the container. The sensors react to the presence of fluid thereby providing an indication of the presence of a leak and the approximate location of the leak.

4 Claims, 6 Drawing Figures

LIQUID CONTAINER LEAKAGE DETECTION METHOD AND SYSTEM

RIGHTS OF THE GOVERNMENT

The invention described herein may be manufactured, used and licensed by or for the United States Government for governmental purposes without the payment to me of any royalties thereon.

BACKGROUND OF THE INVENTION

Minor leaks in liquid containers set into or under the ground surface are extremely difficult to detect. The rate of fluid loss is often slow and variable, particularly if the leak is above the average low liquid level. Also, changes due to natural causes, such as thermal expansion and contraction and evaporation will affect the rate of fluid loss. Frequently, several hundreds of gallons in larger containers must be lost over a period of weeks before the loss is detected. Upon recognition of the problem, costly probing or excavation is generally required in order to actually locate the leak.

As the value of the liquid in question increases, or where the local ecology may be endangered by such leakage it becomes increasingly important to quickly and accurately locate the source of fluid loss. Currently known detection methods are often costly and disruptive of normal operations in the use of storage containers. Some methods, such as the use of radioactive trace materials, introduce their own hazards and are, in any event, useful only when a leak is suspected.

It is therefore an object of this invention to provide a leak detection method for subterranean fluid storage containers which will overcome the disadvantages associated with prior art techniques.

It is an object of the invention to provide a system and method for detecting leaks which is both reliable and economical.

It is a further object of the invention to provide such a detection system which will also enable one to locate the approximate position of a detected leak.

Yet another object of the invention is to provide a leak detection method which is neither harmful to the ecology nor disruptive of the normal use of the fluid storage facility.

SUMMARY OF THE INVENTION

In accordance with the present invention, the integrity of buried fluid containers can be monitored to obtain data showing the presence and approximate location of leaks based on temperature differentials induced in the ground by the leaking fluid. An array of thermal sensors is disposed at a level beneath and throughout the vertical projection of the container, these sensors being intermittently and sequentially scanned to provide data representing the temperature profile of the ground plane beneath the structure. The data is demodulated and compared electronically to determine the presence of a significant temperature gradient. The presence of a gradient may be utilized to initiate an audible or visual warning device.

DESCRIPTION OF A PREFERRED EMBODIMENT

Figure 1:
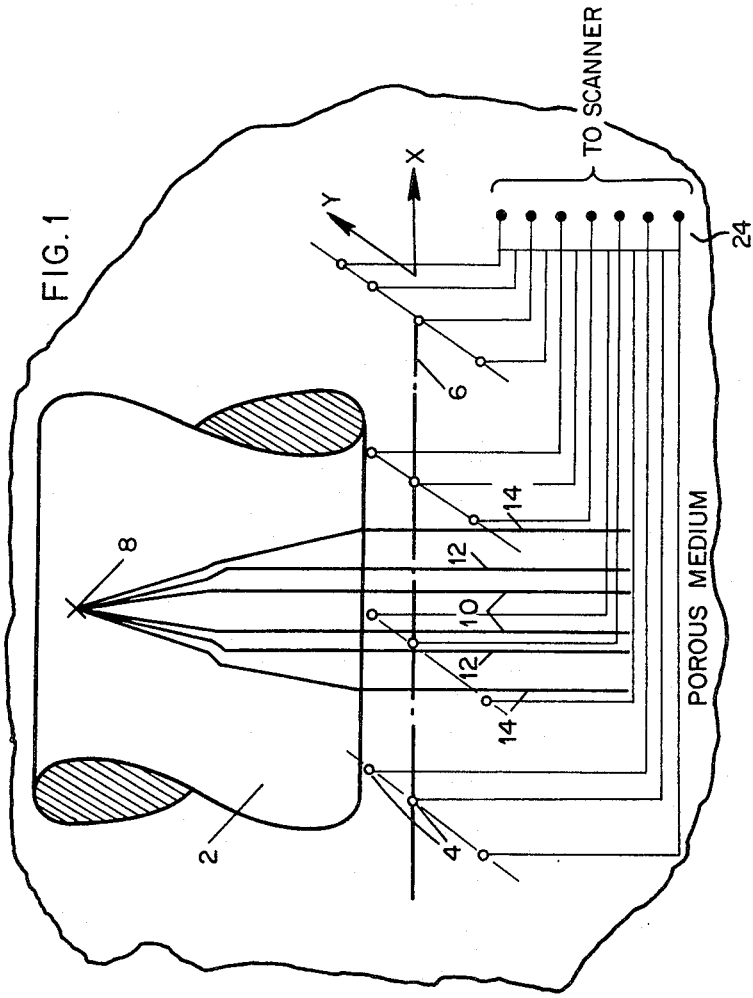
FIG. 1 is a side elevational view of a liquid storage tank associated with an array of sensors in accordance with the present invention.
Figure 2:
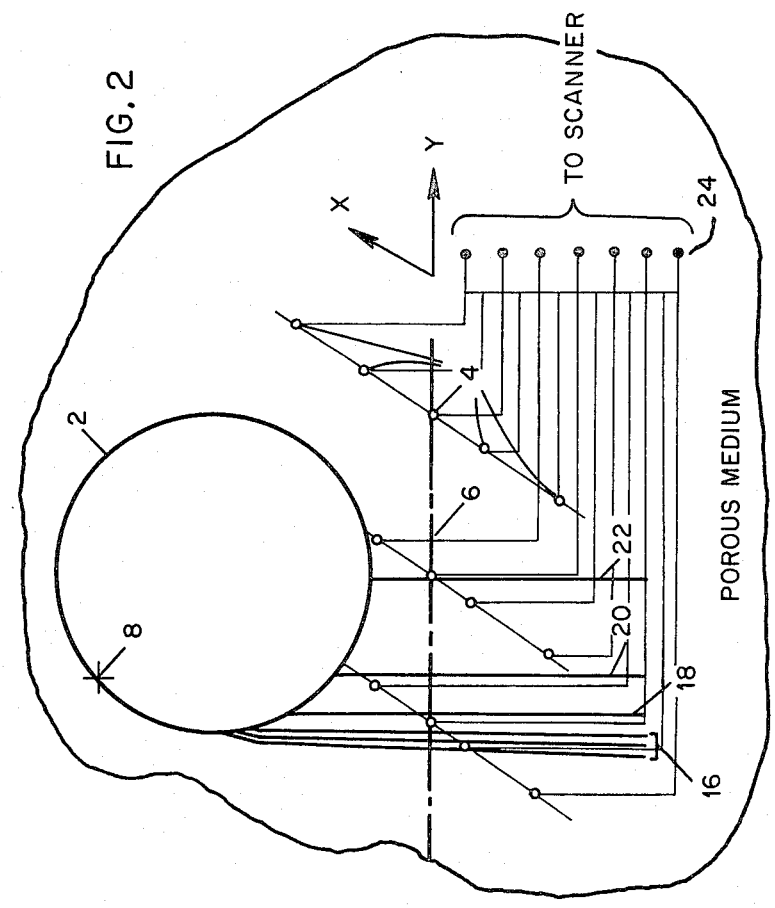
FIG. 2 is an end elevation view of the arrangement of FIG. 1.

Referring to FIGS. 1 and 2, there is shown a side and end view, respectively, of a fluid storage tank 2 which is buried in or under the earth's surface. In a horizontal plane 6, beneath the storage tank, there is arranged an array of sensors 4. The sensors, or detectors, comprise thermistors which upon a change in temperature will exhibit a corresponding change in voltage output.

For the purposes of the following explanation the coordinate direction as seen from left to right in FIG. 1 will be designated the X direction of the horizontal plane 6. Likewise, the coordinate direction as seen from left to right in FIG. 2 will be designated the Y direction of the horizontal plane 6.

As seen in FIGS. 1 and 2, reference numeral 8 designates an exemplary location of a potential leak in the storage tank 2. The flow of the liquid from a leak in the tank is schematically shown by flow lines 10-14 in FIG. 2 and 16-22 in FIG. 3. Along the X direction, as seen in FIG. 1, the path of heaviest flow from the leak will be in a region bounded approximately by flow lines 10. Moving outwardly in either direction from this region toward to flow lines 12 the total flow diminishes. The flow is diminished to an even greater extent in the region of flow lines 14.

Figure 3:
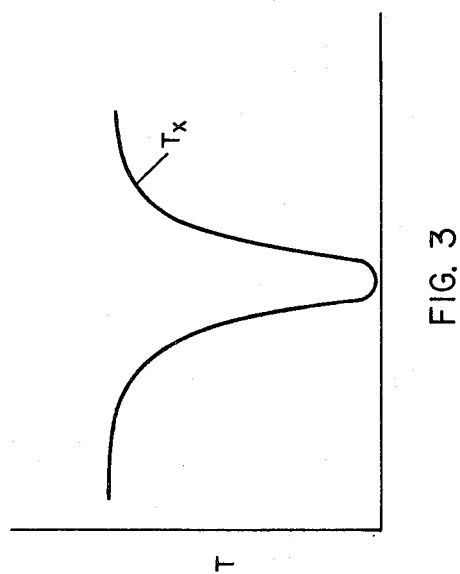
FIGS. 3 and 4 are graphical illustrations of the temperature gradients along the array, as shown in FIGS. 1 and 2 respectively, induced by a leak from the storage tank.

The fluid flow through the porous medium induces a temperature change in the medium. The extent of the temperature change is proportional to the amount of flow. Therefore, the thermistors 4 located in the region of heaviest flow will show a more substantial change in temperature than the thermistors, located in a region of lighter flow or no flow. A scanning of the sensors along the X direction will yield a temperature distribution substantially as seen in FIG. 3. The thermistors in the region of flow lines 10 exhibit a substantial decrease in temperature, thus indicating the most likely position of the leak in the X direction.

Referring to FIG. 2, it will be evident that the heaviest flow from leak 8 will be in the region of flow lines 16, the extent of flow diminishing as one moves outwardly toward flow lines 18, 20 and 22 in succession. Again, the sensors located in the region of heaviest flow will exhibit the greatest change in temperature. The temperature distribution in the Y direction, as graphically illustrated in FIG. 4, will indicate a most likely location of the leak in the Y direction.

By correlating the positions of the most severe temperature deviations, one will have an indication of the most likely position of the leak from the storage tank. If the leak is located on the lower-most portion of the tank, the most pronounced temperature deviation will occur at a point which is substantially directly below the leak. If a leak occurs on the upper-most portion of the tank, as indicated in FIGS. 1 and 2, run-off over the top portion of the tank will cause the temperature deviation to occur at a position generally below the outermost edge of the storage vessel, as in the example given above.

As previously indicated, the detectors or sensors comprise thermistors. It is essential, of course, that these thermistors be water-proof. Beyond this, the type of thermistor utilized is a matter of choice, and may be chosen on the basis of such factors as cost or availability.

The spacing of the sensors is variable. The more sensors that are provided, the greater will be the accuracy of the system in locating an existing leak. Also, more closely spacing the sensors will yield an earlier warning of a leak. Again, cost may be a factor in determining how many sensors to provide for any particular system.

Figure 5:
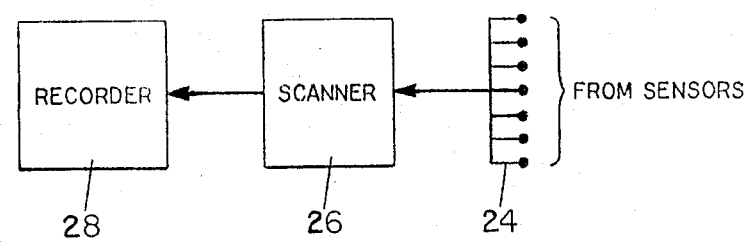
FIGS. 5 and 6 schematically illustrate two variations of data processing systems which may be utilized to gather and analyze data from the sensors of the present invention.

The sensors may be advantageously arranged in a matrix-like array under the storage vessel. Data may be sequentially gathered from the respective sensors in order to determine the temperature throughout the entire plane. 6. Scanning means, such as that disclosed in U.S. Pat. No. 3,936,839, may be provided for this purpose. As shown in FIG. 5, data gathered from the sensors by means of connections 24 is fed to the scanner 26. This data may be simply relayed in an organized fashion to a recorder 28 which will provide a descriptive and useful record of the data. This may be, for example, a strip chart recorder or merely numerical data printed out.

Figure 6:
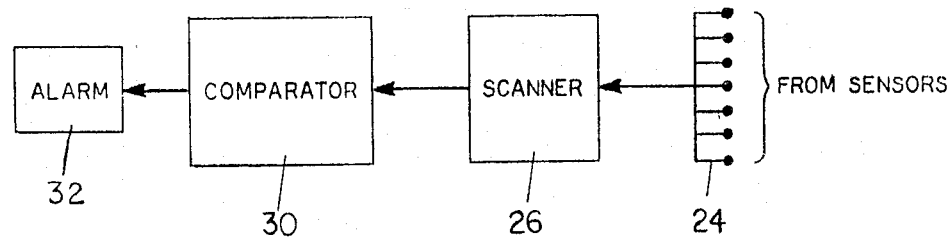

FIG. 6 illustrates an alternative system for managing the data gathered from the sensors. Information gathered by means of connectors 24 and scanner 26 is relayed to a comparator 30. The voltage levels from the respective thermistor sensors are compared with one another by the comparator means 30. A determination is made of the greatest absolute difference among the various sensors. This difference is then compared to a present average level of output of the thermistors. If one or more of the sensors exhibits a substantial deviation from the average output, the system initiates a visual or audible alarm signal 32. This deviation from the average output will be indicative of a leak causing a temperature deviation at at least one location within plane 6.

Figure 4:
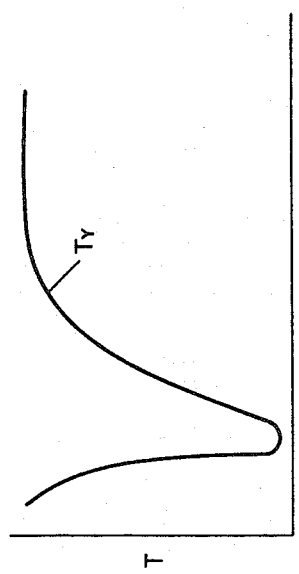

A comparison of the conditions of the various sensors is necessary to determine if a leak exists. This is due to the fact that such external conditions, such as heavy rainfall, will result in a change in subsurface temperature at the location of each sensor 4. Therefore, a change in temperature of all sensors is likely to indicate a condition such as a change in the average moisture content of the ambient soil. A leak from the storage container will result in a local variation, causing a temperature gradient such as shown in FIGS. 3 and 4.

While the present invention has been described with relation to a storage tank, as seen in FIGS. 1 and 2, it is to be understood that it is not limited to such a combination. The apparatus and method of the present invention finds use in combination with such things as swimming pools, sewerage lagoons, pipelines, etc. Therefore, while the invention has been described with relation to the accompanying drawings, I do not desire to be limited to the details shown therein as obvious modifications may be made by one of ordinary skill in the art.

I claim:

1. A system for detecting fluid leakage from a container located in a porous medium, comprising:

an array of thermistors arranged in a horizontal plane beneath said container in said porous medium;

means for sequentially and intermittently scanning said array to detect electrical signals from each of said thermistors indicative of an individual temperature of each of said thermistors;

means for determining an average temperature from said electrical signals indicative of an average temperature of said horizontal plane; means for comparing each of said individual temperatures of each of said thermistors represented by said electrical signals to said average temperature of said horizontal plane to detect the existence of a substantial temperature deviation indicated by one or more of said thermistors from said average;

means for comparing said temperature deviations to determine differential temperatures between two or more adjacent thermistors;

means for determining a temperature gradient from said differential temperatures whereby a position of said leak is determined from a maximum temperature deviation indicated by said temperature gradient; and means for generating a signal to activate an alarm when said leak is detected.

2. A system, as recited in claim 1, wherein said means for determining a temperature gradient comprises:

means for determining a first position of a maximum temperature deviation from said differential temperatures in a first direction;

means for determining a second position of a maximum temperature deviation from said differential temperatures in a second direction wherein said second direction is orthogonal to said first direction; and means for correlating said first position with said second position relative to said container to determine the location of said leak.

3. A system, as recited in claim 2, wherein said alarm comprises an audible warning system.

4. A system, as recited in claim 2, wherein said alarm comprises a visible warning system.

* * * * *